United States Patent
Nearman et al.

(10) Patent No.: US 8,460,184 B2
(45) Date of Patent: Jun. 11, 2013

(54) AIRWAY MANAGEMENT

(75) Inventors: Howard S. Nearman, Pepper Pike, OH (US); Donald M. Voltz, Twinsburg, OH (US); Alon S. Aharon, Scarsdale, NY (US)

(73) Assignees: University Hospitals of Cleveland, Cleveland, OH (US); Turocy & Watson, LLP, Cleveland, OH (US)

( * ) Notice: Subject to any disclaimer, the term of this patent is extended or adjusted under 35 U.S.C. 154(b) by 530 days.

(21) Appl. No.: 12/636,271

(22) Filed: Dec. 11, 2009

(65) Prior Publication Data

US 2011/0144436 A1 Jun. 16, 2011

(51) Int. Cl.
*A61B 1/267* (2006.01)

(52) U.S. Cl.
USPC .......................................... 600/188

(58) Field of Classification Search
USPC ................. 600/166–177, 188–190, 194, 196, 600/223, 225, 239, 240
See application file for complete search history.

(56) References Cited

U.S. PATENT DOCUMENTS

| | | | |
|---|---|---|---|
| 3,913,568 A * | 10/1975 | Carpenter | 600/142 |
| 4,337,761 A | 7/1982 | Upsher | |
| 4,573,451 A * | 3/1986 | Bauman | 600/190 |
| 5,840,013 A | 11/1998 | Lee | |
| 6,053,166 A | 4/2000 | Gomez | |
| 6,543,447 B2 | 4/2003 | Pacey | |
| 6,655,377 B2 * | 12/2003 | Pacey | 128/200.26 |
| 6,843,769 B1 | 1/2005 | Gandarias | |
| 6,991,604 B2 | 1/2006 | Cantrell | |
| 7,089,928 B2 | 8/2006 | Besharim et al. | |
| 2002/0022769 A1 | 2/2002 | Smith et al. | |
| 2004/0215061 A1 | 10/2004 | Kimmel et al. | |
| 2006/0020171 A1 * | 1/2006 | Gilreath | 600/188 |
| 2006/0122475 A1 | 6/2006 | Balberg et al. | |
| 2006/0221191 A1 | 10/2006 | Nonaka et al. | |
| 2007/0038023 A1 | 2/2007 | Uchimura et al. | |
| 2007/0129603 A1 | 6/2007 | Hirsh | |
| 2007/0179342 A1 | 8/2007 | Miller et al. | |
| 2009/0209826 A1 * | 8/2009 | Sanders et al. | 600/188 |

FOREIGN PATENT DOCUMENTS

| | | |
|---|---|---|
| DE | 29921801 U | 3/2000 |
| EP | 1285623 A1 | 2/2003 |
| FR | 2821736 A1 | 9/2002 |
| JP | 2003-117000 | 4/2003 |
| JP | 2005-334462 | 12/2005 |

(Continued)

OTHER PUBLICATIONS

CN OA dated Sep. 21, 2011 for Chinese Application No. 200880103408.4, 9 pages.

(Continued)

*Primary Examiner* — Eduardo C Robert
*Assistant Examiner* — Tara Carter
(74) *Attorney, Agent, or Firm* — Turocy & Watson, LLP

(57) ABSTRACT

The claimed subject matter provides systems and/or methods that facilitate improving visualization associated with intubation. A dynamically articulating laryngoscope blade can be controlled to configure to normal anatomic variants and pathologic abnormalities to facilitate placing of an endotracheal tube into a patient's trachea. Further, cameras can be integrated into and/or mounted upon the dynamically articulating laryngoscope blade. The cameras can enable stereoscopic visualization of the laryngeal aperture allowing for depth perception. Moreover, the cameras can be moved independently of the blade allowing for optimal viewing of the laryngeal opening.

12 Claims, 12 Drawing Sheets

FOREIGN PATENT DOCUMENTS

| | | |
|---|---|---|
| JP | 2006-000282 | 1/2006 |
| JP | 2006-198031 | 8/2006 |
| JP | 2007503931 | 3/2007 |
| KR | 1019990087101 | 12/1999 |
| WO | 93/11700 | 6/1993 |
| WO | 97/30626 | 8/1997 |
| WO | 02/11608 | 2/2002 |
| WO | 2004/000107 | 12/2003 |

OTHER PUBLICATIONS

Australian OA dated Nov. 30, 2011 for Australian Patent Application No. 2008266236, 3 pages.
Japanese OA dated Nov. 21, 2011 for Japanese Patent Application No. 2010-512319, 3 pages.
European OA dated Dec. 16, 2011 for EP Patent Application No. 08770700.6, 6 pages.
International Search Report dated Nov. 22, 2008 mailed Dec. 9, 2008 for PCT Application Serial No. PCT/US 08/66544, 13 Pages.
Australian Office Action for Australian Application No. 2008-266236, dated Nov. 8, 2010, 2 pages.
Korean OA dated Mar. 31, 2011 for Korean Patent Application No. 10-2010-7000584, 7 pages.
Canadian OA dated Mar. 21, 2012 for Canadian Patent Application No. 2689676, 3 pages.
Office Action mailed Jun. 19, 2012 for U.S. Appl. No. 12/754,362, 30 pages.
CN OA dated Jul. 31, 2012 for Chinese Application No. 200880103408.4, 10 pages.
Japanese OA, mailing date Jul. 31, 2012 for JP Application No. 2010-512319, 3 pages.
Israel OA dated Jun. 25, 2012 for Israel Patent Application No. 202541, 5 pages (untranslated OA issued in foreign counterpart application).
European Office Action for European Patent Application No. 08770700.6-2319 dated Dec. 4, 2012, 4 pages.
EP Search Report for European Application No. 08770700.6-2319 /2155040 dated Jun. 7, 2010, 7 pages.

* cited by examiner

Laryngeal aperture (opening into trachea)

AIRWAY MANAGEMENT

CROSS-REFERENCE TO RELATED APPLICATIONS

This application is a U.S. national stage filing of Patent Cooperation Treaty (PCT) application serial number PCT/US08/66544 entitled "AIRWAY MANAGEMENT" filed Jun. 11, 2008, which claims the benefit of U.S. Provisional Patent Application Ser. No. 60/943,320 entitled "AIRWAY MANAGEMENT" filed Jun. 12, 2007. The entireties of the aforementioned applications are herein incorporated by reference.

BACKGROUND

Medical endoscopy has continued to advance with increasing sophistication in both camera and illumination technology. The area of airway management has also embraced technological advances in optics and light transmission resulting in development of numerous devices to assist a medical provider with placement of a breathing tube into the trachea of a patient requiring mechanical ventilatory assistance (e.g., endotracheal intubation).

An area of airway management which has not seen much advancement since the introduction of peroral endotracheal intubation in the 18th century is the design of the laryngoscopic instrument used to displace the tongue and allow for visualization of vocal cords and laryngeal aperture. A number of subtle changes have been implemented in these tools resulting in many different variations in the laryngoscopic blade. These devices, although quite varied in design, are placed into the oral cavity and used to forcefully move the tongue, mandible, and connected soft tissue out of the way allowing for visualization of the tracheal inlet. This maneuver can be highly stimulating to patients necessitating some form of anesthesia to tolerate its use. In addition, even with increasing levels of force applied to the device, there are patients with anatomical variants or pathologic conditions that do not allow direct visualization of the tracheal opening.

In the United States, it has been estimated that 10 million people undergo general anesthesia each year for a variety of operations. During the induction of general anesthesia, a significant percentage of patients require placement of an endotracheal tube along with mechanical ventilation to overcome cessation of breathing caused by anesthetic medications. The process of placing an endotracheal tube into the trachea varies in difficulty depending on a patient's body habitus, variations in normal anatomy, as well as variations in anatomic deviations as a result of numerous pathologic processes. Placement of the endotracheal tube depends both on the skills of the anesthesiologist as well as the instruments used to visualize the opening of the trachea. In a normal anesthetic situation, once a patient is placed under general anesthesia, a rigid laryngoscope can be placed into the mouth to displace the tongue allowing for exposure of the laryngeal aperture. Once the larynx is visualized, an endotracheal tube can be placed into the trachea and a high volume, low pressure cuff can be inflated to provide a seal between the endotracheal tube and the inner wall of the trachea. Numerous risks and complications can occur with the placement of an endotracheal tube, risks that increase in patients with abnormal body habitus (such as morbid obesity), or variations in normal anatomy as the result of congenital or pathologic conditions. Thus, anesthesiologists desire to quickly, reliably and safely place an endotracheal tube after anesthetic induction to mitigate chances of the patient becoming hypoxic (e.g., lack of oxygen in the blood) resulting in injury to systems in the body, especially the heart and the brain. For example, it has been estimated that intubation problems account for about one third of all deaths and serious injuries related to anesthesiology. In addition, many more patients are placed at risk outside the operating room. For instance, emergent placement of an endotracheal tube can be encountered when a patient experiences cardiac and/or respiratory arrest, both inside and outside the hospital setting. A challenge for anesthesiologists as well as other health care providers who have specialty training in the area of airway management is to place the endotracheal tube in a position far removed from where they are visualizing it (e.g., viewing from the mouth opening for traditional laryngoscopy).

SUMMARY

The following presents a simplified summary in order to provide a basic understanding of some aspects described herein. This summary is not an extensive overview of the claimed subject matter. It is intended to neither identify key or critical elements of the claimed subject matter nor delineate the scope thereof. Its sole purpose is to present some concepts in a simplified form as a prelude to the more detailed description that is presented later.

The claimed subject matter relates to systems and/or methods that facilitate improving visualization associated with intubation. A dynamically articulating laryngoscope blade can be controlled to configure to normal anatomic variants and pathologic abnormalities to facilitate placing of an endotracheal tube into a patient's trachea. Further, cameras can be integrated into and/or mounted upon the dynamically articulating laryngoscope blade. The cameras can enable stereoscopic visualization of the laryngeal aperture allowing for depth perception. Moreover, the cameras can be moved independently of the blade allowing for optimal viewing of the laryngeal opening.

In accordance with various aspects of the claimed subject matter, data observed from the oral cavity can be retained in a data store. For example, videos and/or images can be collected within the data store associated with an airway management apparatus (e.g., laryngoscope). Further, the videos and/or images can be archived when the apparatus is placed in a cradle (e.g., uploaded to a hospital server). Additionally or alternatively, the videos and/or images can be retained upon memory (e.g., flash) that can be removed from the apparatus (e.g., and included in a patient's file, used for training/documentation purposes, . . . ).

Pursuant to one or more aspects of the claimed subject matter, collected data can be wirelessly transmitted to a disparate device for real time presentation. For example, the videos and/or images can be wireless transmitted from the apparatus to a disparate device capable of presenting a corresponding output. Therefore, while the laryngoscope is positioned within the oral cavity, feedback can be output to the user of the laryngoscope (and/or any disparate user). It is contemplated that any type of wireless communication technology can be leveraged to communicate the collected data to the disparate device. Further, control of the articulating blade and/or cameras can be obtained from the disparate device via the wireless communication.

The following description and the annexed drawings set forth in detail certain illustrative aspects of the claimed subject matter. These aspects are indicative, however, of but a few of the various ways in which the principles of such matter may be employed and the claimed subject matter is intended to include all such aspects and their equivalents. Other advan-

DETAILED DESCRIPTION

Figure 1:
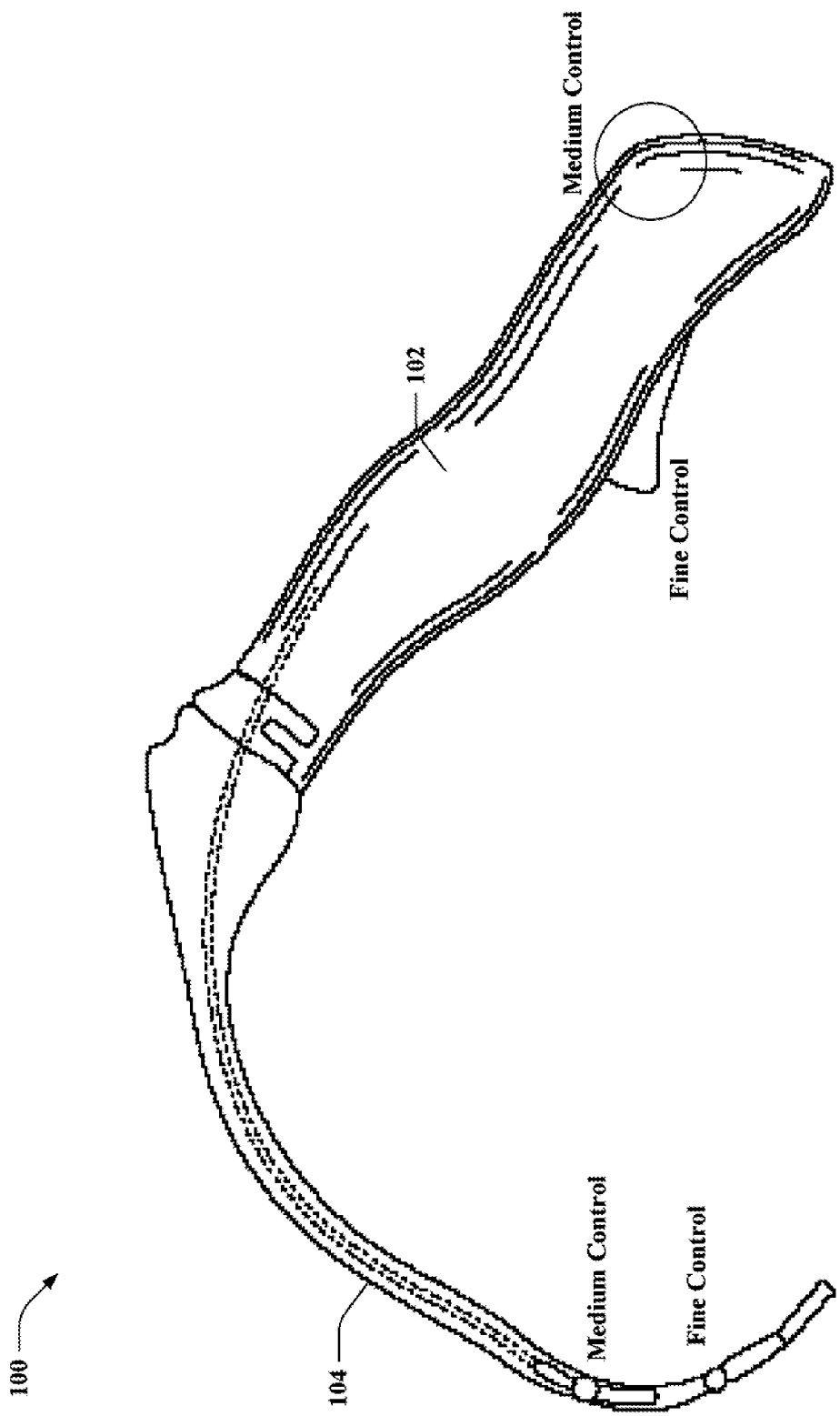
FIG. 1 illustrates an example schematic of an airway management apparatus in accordance with various aspects of the claimed subject matter.

The claimed subject matter is described with reference to the drawings, wherein like reference numerals are used to refer to like elements throughout. In the following description, for purposes of explanation, numerous specific details are set forth in order to provide a thorough understanding of the subject innovation. It may be evident, however, that the claimed subject matter may be practiced without these specific details. In other instances, well-known structures and devices are shown in block diagram form in order to facilitate describing the subject innovation.

As utilized herein, terms "component," "system," and the like are intended to refer to a computer-related entity, either hardware, software (e.g., in execution), and/or firmware. For example, a component can be a process running on a processor, a processor, an object, an executable, a program, and/or a computer. By way of illustration, both an application running on a server and the server can be a component. One or more components can reside within a process and a component can be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. For example, computer readable media can include but are not limited to magnetic storage devices (e.g., hard disk, floppy disk, magnetic strips, . . . ), optical disks (e.g., compact disk (CD), digital versatile disk (DVD), . . . ), smart cards, and flash memory devices (e.g., card, stick, key drive, . . . ). Additionally it should be appreciated that a carrier wave can be employed to carry computer-readable electronic data such as those used in transmitting and receiving electronic mail or in accessing a network such as the Internet or a local area network (LAN). Of course, those skilled in the art will recognize many modifications may be made to this configuration without departing from the scope or spirit of the claimed subject matter. Moreover, the word "exemplary" is used herein to mean serving as an example, instance, or illustration. Any aspect or design described herein as "exemplary" is not necessarily to be construed as preferred or advantageous over other aspects or designs.

Now turning to the figures, FIG. 1 illustrates an example schematic of an airway management apparatus 100 in accordance with various aspects of the claimed subject matter. It is to be appreciated that the claimed subject matter is not limited to the depicted example schematic. The apparatus 100 can enable placement of an endotracheal tube during induction of general anesthesia and/or for emergency management of the airway during any type of respiratory embarrassment in a controlled operating room environment, other hospital location such as the emergency department, or outside the hospital in any number of field situations. For example, the apparatus 100 can include one or more cameras that can be maneuvered in close proximity to the opening of the trachea. By allowing maneuvering of the one or more cameras, a health care provider employing the apparatus 100 can have an increased chance of appropriately placing an endotracheal tube. Further, the apparatus 100 can provide direct, visual feedback that the endotracheal tube is in a proper place, and thus, mitigate adverse events associated with a misplaced tube.

The apparatus 100 can be a self-contained single piece. For instance, the apparatus 100 can include a handle 102 and a blade 104. As such, the apparatus 100 can have similarity to a conventional Macintosh laryngoscope with notable variations as discuss below. According to another example, the blade 104 can be removable from the handle 102 of the apparatus 100 and/or replaceable (e.g., the blade 104 or a portion thereof can be disposable); however, the blade 104 need not be removable from the handle 102 and/or replaceable. It is contemplated that blades of various sizes, shapes, thicknesses, material compositions, etc. can be attached to a common handle, for instance. According to another illustration, it is to be appreciated that the handle 102 can be a universal handle; as such, the handle 102 can interchangeably connect with the blade 104 and/or any disparate type of device (e.g., bronchoscope, ENT Dido scope, . . . ) while providing similar functionality (e.g., power source, wireless communication, data storage, . . . ) as described below to each of these disparate types of devices. Such a universal handle 102 can be portable. Further, the universal handle 102 can include servo-control capabilities that can effectuate operating substantially any type of device to which the handle 102 is attached. Moreover, the universal handle 102 can enable acquisition, archiving, transmission (e.g., wireless, wired, . . . ), generation of reports, etc. related to data associated with the attached device (e.g., the blade 104, bronchoscope, ENT Dido scope, mediastinoscope, colonoscope, . . . )

as described below. For example, data can be obtained via the device attached to the universal handle 102 by way of fiberoptics, cameras, ultrasound, and/or substantially any type of sensor(s).

The blade 104 can be a dynamically articulating laryngoscope blade that can be controlled to configure to normal anatomic variants as well as pathologic abnormalities to facilitate placing an endotracheal tube into the trachea. Thus, the blade 104 can accommodate variation in normal and abnormal anatomy of the upper airway resulting in less airway trauma and stimulation stress on a patient undergoing intubation. In contrast to conventional blades that commonly have fixed curvature, the blade 104 can be controlled via the handle 102 to adjust the curvature, manipulate portions or the entire blade 104 relative to the handle 102, etc. Accordingly, the apparatus 100 can be slid along the handle 102 to lengthen or shorten the blade. Further, upon obtaining the proper blade length, the blade 104 can be flexed up or down via a medium control to provide a crude view of the vocal cords (e.g., camera(s) can be positioned nearby the medium control articulation point). Additionally, a tip of the blade 104 can be manipulated via a fine control to alter the position of a patient's epiglottis to provide a clearer view of the vocal cords. It is contemplated that the blade 104 can be manipulated at any disparate location(s) upon the blade 104 other than or in addition to those depicted in the illustrated schematic.

The blade 104 can also have one or more digital cameras (e.g., stereoscopic cameras) mounted thereupon. The digital camera(s) can be moved independently of the blade 104, for instance, to allow for optimal viewing of the laryngeal opening. Further, articulation of the blade 104 can enable positioning the camera(s) such that an unobstructed view of the vocal cords can be obtained. It is to be appreciated that the camera(s) can be integrated into the blade 104, attached to the blade 104 (e.g., permanently, temporarily, . . . ), and so forth. According to an example, the camera(s) can be removeably connected to the blade 104 thereby allowing for replacement.

The handle 102 can include a power supply. For instance, the power supply can be a battery (e.g., a lithium-battery). Additionally, the handle 102 can comprise an interface that enables connecting to a cradle. When connected to (e.g., docked upon) the cradle, the power supply can be recharged, digital images and/or video obtained by the one or more digital cameras can be transferred, and so forth. In addition, the apparatus 100 (e.g., the handle 102) can include an integrated processor. By way of illustration, the processor can control operation associated with the one or more digital cameras; thus, the processor can enable capturing digital images and/or video with the camera(s) and/or transferring the captured data to a remote location (e.g., via the interface when connected to the cradle, a wireless connection, . . . ).

The handle 102 can also include controls that allow for manipulation of the articulating blade 104. The differing controls can provide varying precision of manipulation (e.g., medium control, fine control, . . . ). By way of illustration, the controls included with the handle 102 can mechanically alter the size, shape, curvature, orientation, etc. of the blade 104. Additionally or alternatively, the controls can transmit a signal that can initiate such alterations (e.g., employing a servo motor). Also, the handle 102 can comprise a control that releases the integrated channel for passage of the endotracheal tube or other airway device.

The attached blade 104 can be constructed of a plurality of flat metal blades that articulate on one another allowing for the blade 104 to dynamically assume multiple configurations depending on the patient's airway anatomy. Thus, the blade 104 can include multiple articulating plates that allow the blade 104 to flex throughout its length as well as at the tip. The control apparatus for this manipulation can be positioned within the handle 102.

The apparatus 100 can provide a number of advantages as compared to conventional devices. Every patient has a different anatomically structured airway and securing an airway can be difficult. The apparatus 100 can mitigate such difficulty by producing a reasonable view of the tracheal inlet thereby allowing for placement of an endotracheal tube. Additionally, the curvature of the laryngoscopic blade 104 can change in real time while in the oral cavity via the controls to accommodate for normal variations in airway anatomy or pathologic airway conditions (e.g., tumors). By allowing for variation in the curvature of the blade 104 while within the oral cavity, changing the blade 104 to provide for variations in size and/or shape need not occur (e.g., reducing intubation time, . . . ). Further, trauma to the upper airway can be reduced by employing the apparatus 100 and the physiologic stress on the patient associated with applying force on the tongue and oral cavity tissues can be lessened through a more efficient utilization of force and viewing angles. Moreover, the ability to visualize the vocal cords is often obstructed by the epiglottis covering the tracheal opening when employing conventional devices. In order to effectively overcome this obstacle, one can place the laryngoscope blade under the epiglottis to bring it out of the way or anteriorly displace the epiglottis by applying anteriorly directed force in the velecula, elevating the epiglottis with the adjoining soft tissue. Traditional laryngoscopes oftentimes fail to do this since to apply anterior force in the velecula requires the operator to "hinge" back on the blade, driving the proximal end of the blade into the patient's incisors. This can result in injury to the teeth, oral mucosa, or cause trauma to the lower part of the airway with adequately improving the view of the tracheal opening. In contrast, the portion of the blade 104 associated with fine control (e.g., tip of the blade 104) can pull the epiglottis out of the way to allow for viewing the vocal cords.

In addition to difficulty associated with visualization of the laryngeal aperture, once the anesthesia provider obtains a view, it is sometimes difficult to maneuver the endotracheal tube into the trachea to complete the process of securing an airway while employing conventional techniques. The apparatus 100 can mitigate the maneuvering related difficulty by having a channel positioned along the side of the blade 104 that can include a ball bearing and spring-loaded pusher plate to dynamically adapt to variously size endotracheal tubes or airway intubation stylets. The channel can be positioned and/or adapt its position as the blade 104 articulates to deliver the tip of the endotracheal tube to the center of the camera viewing apparatus. This allows the operator to center the laryngeal aperture and watch under direct vision as the endotracheal tube passes into the trachea.

Moreover, in certain situations, patients may present with a physical exam that deems them as very challenging airways because of anatomic changes or pathologic tumors. In these situations, patients may need to have their airways secured without the addition of any anesthetic medications that may lead to sedation and a cessation of breathing or an obstruction of the patent airway that they initially presented with making things more urgent and often more difficult and stressful on the patient. Applying local anesthetics to these specific airways allows for the anesthesiologist to place a fiberoptic camera or gently place a laryngoscope to determine if it is safe to place the patient asleep prior to placing a breathing tube. The apparatus 100 can have a channel that operates using Bernoulli principles to atomize liquid local anesthetic medications. This coupled with the camera system can allow one to completely topicallize the airway while the device is being placed resulting in a much more comfortable state of the patient as well as maintaining a spontaneously breathing state.

According to another example, a sleeve-type cover can be placed over the blade 104 and/or the handle 102 to enable reuse of the device without cleaning. According to an illustration, the sleeve-type cover can be disposable; however, it is to be appreciated that the cover can be sterilized to allow for reuse of the cover. Moreover, the cover can allow for the blade 104 to be articulated as well as data to be collected (e.g., via the cameras attached to the blade 104, . . . ) while mitigating obstruction thereof.

Figure 2:
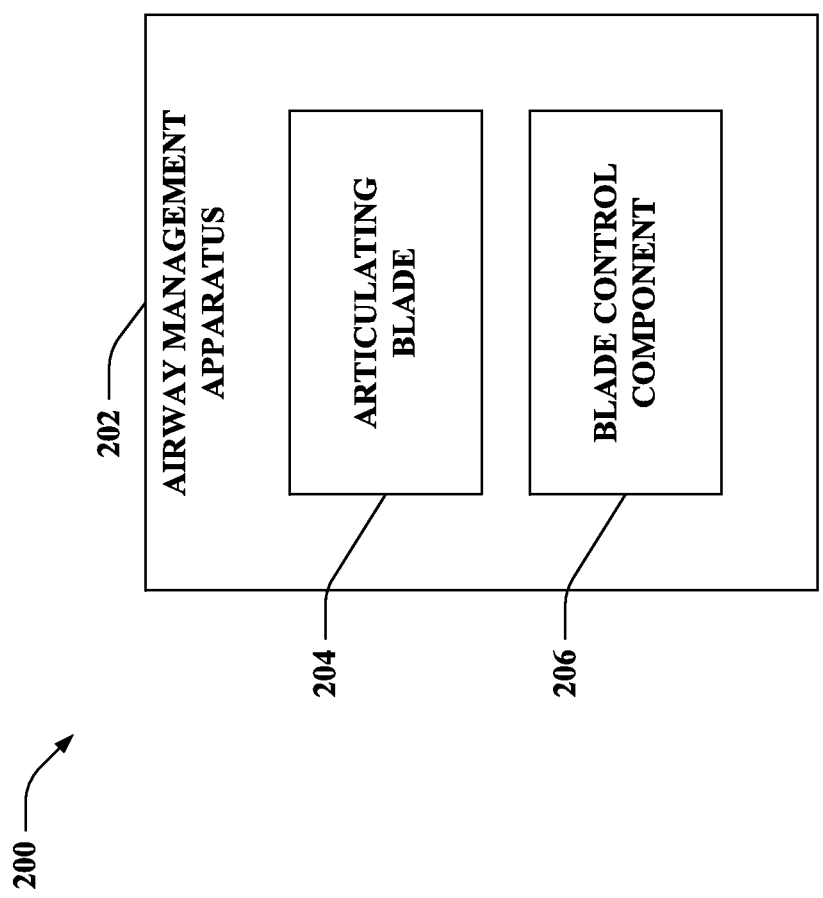
FIG. 2 illustrates a block diagram of an exemplary system that facilitates intubating a patient.

Turning to FIG. 2, illustrated is an example system 200 that facilitates intubating a patient. The system 200 includes an airway management apparatus 202 (e.g., the apparatus 100 of FIG. 1) that enables performing direct laryngoscopy. The airway management apparatus 202 further includes an articulating blade 204 (e.g., the blade 104 of FIG. 1) and a blade control component 206 (e.g., included in the handle 102 of FIG. 1).

The articulating blade 204 can be manipulated in any manner. For instance, the size, length, shape, curvature, and the like of the articulating blade 204 or portion(s) thereof can be changed. By way of example, in contrast to some conventional devices with blades that have a fixed curvature, the curvature of the articulating blade 204 can be altered based upon anatomic characteristics of a patient. Further, such adjustments can be effectuated while positioning the airway management apparatus 202 proximate to the trachea within the oral cavity (e.g., as opposed to altering these features while the apparatus is removed from the patient's mouth and thereafter positioning the apparatus). The articulating blade 204 can accommodate variation in normal and abnormal anatomy of the upper airway. Moreover, the articulating blade 204 can reduce airway trauma and stimulation stress on the patient undergoing intubation. Additionally, the articulating blade 204 can be thinner than conventional blades employed in connection with typical laryngoscopic devices.

The articulating blade 204 can have any number of articulation points that can allow for varying degrees of control. For instance, a first articulation point can allow for crudely obtaining a view of the vocal cords (e.g., by adjusting an angle of camera(s) to be directed at the vocal cords from the base of the tongue). Further, a second articulation point can improve the crude view by manipulating the epiglottis of the patient.

The blade control component 206 can enable manipulating the articulating blade 204. The blade control component 206 can be included in a handle (e.g., the handle 102) of the airway management apparatus 202. The blade control component 206 can obtain substantially any type of input to yield a corresponding alteration of the articulating blade 204. For example, the blade control component 206 can receive an input from a user of the airway management apparatus 202 (e.g., via a button, joystick, switch, lever, touch screen, voice command, sensor, mouse, trigger, . . . ). According to another illustration, an input can be provided from a remotely located user via a signal; thus, telemedicine can be performed such that a user other than a user physically touching the airway management apparatus 202 can provide input utilized to manipulate the articulating blade 204. Moreover, the blade control component 206 can adjust the articulating blade 202 mechanically, via an electrical signal, and so forth. By way of illustration, the input can be utilized to control one or more motors to manipulate the articulating blade 202. For instance, servo motor(s) can leverage the input to smoothly control movement of the articulating blade 202 in substantially any number of planes. Additionally or alternatively, linear motor(s) can employ the input to manipulate the articulating blade 202. Thus, according to an example, the blade control component 206 can receive a user input, which can control servo motor(s) and/or linear motor(s) that can elongate, shorten, alter elevation, etc. associated with the articulating blade 204 or a portion thereof.

The articulating blade 204 can further include an adaptable channel (not shown). The adaptable channel can be adjusted in a size, shape, etc. (e.g., while the airway management apparatus 202 is being employed upon a patient). Also, the adaptable channel can allow for secure and directional placement of variously sized endotracheal tubes, intubating stylets, jet ventilation equipment, and the like. The adaptable channel can be employed to facilitate passing an endotracheal tube into the trachea under direct vision, for example.

The articulating blade 204 can also include a light transmission component (not shown) that can illuminate a patient's airway. For instance, controls (e.g., that alter on/off state, intensity, direction, wavelength, . . . ) for the light transmission component can be included in the handle of the airway management apparatus 202. Moreover, the light transmission component can be permanently affixed to, incorporated into, temporarily attached to (e.g., removable, replaceable, . . . ), etc. the articulating blade 204. Further, the articulating blade 204 can comprise an airway atomizing device, which can be used to deliver topical anesthesia during placement of an endotracheal tube.

Figure 3:
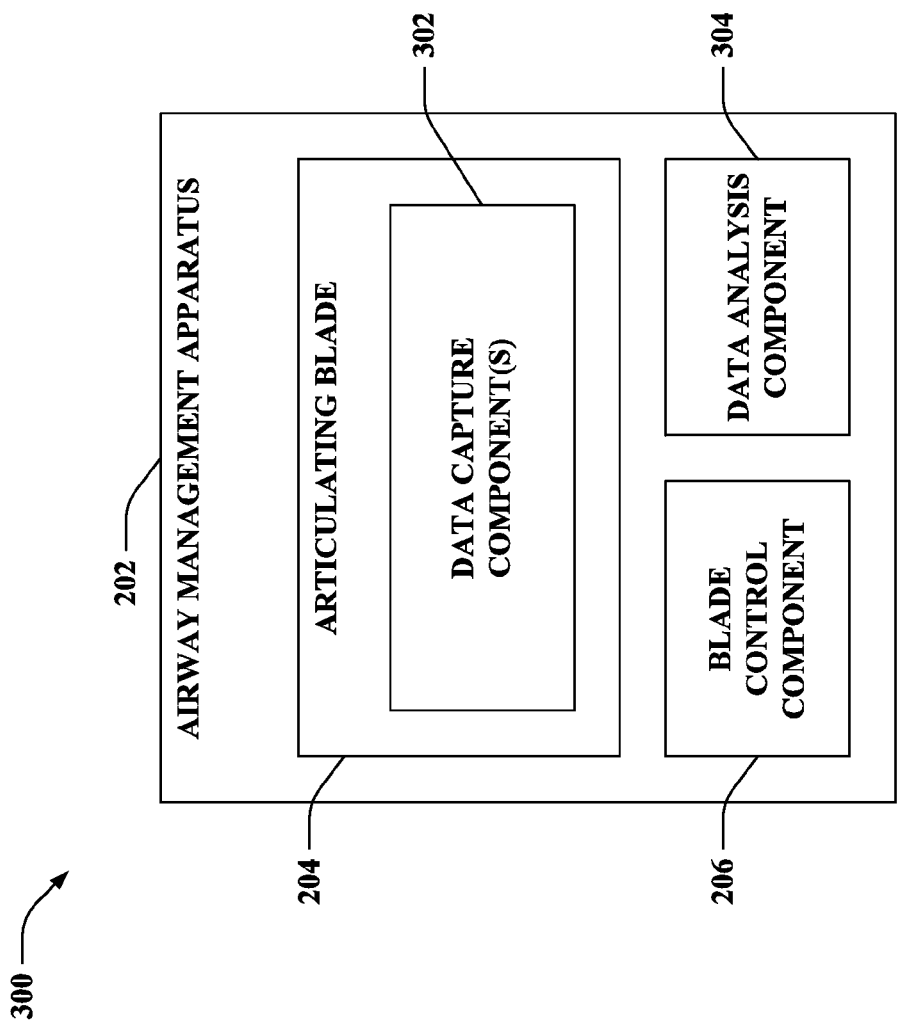
FIG. 3 illustrates a block diagram of an exemplary system that enables performing video laryngoscopy in accordance with various aspects.

Now turning to FIG. 3, illustrated is an example system 300 that enables performing video laryngoscopy in accordance with various aspects. The system 300 includes the airway management apparatus 202, which can further comprise the articulating blade 204 and the blade control component 206. The articulating blade 204 can also include data capture component(s) 302 that collect substantially any type of data (e.g., visual, audio, chemical, pressure, temperature, . . . ). It is contemplated that any number and/or type of data capture component(s) 302 can be utilized in connection with the airway management apparatus 202. A data analysis component 304 can further employ (e.g., aggregate, evaluate, . . . ) the data obtained by the data capture component(s) 302.

According to an example, the data capture component(s) 302 can be a plurality of cameras (e.g., two, more than two, . . . ) that can provide a stereoscopic view. The cameras can be located upon the articulating blade 204 at an articulation point that can be positioned at the base of the tongue looking up when the apparatus 202 is utilized upon a patient. Thus, as opposed to conventional techniques where the vocal cords are viewed from outside of the mouth, the cameras can capture a view from the base of the tongue. The cameras can be any type of digital cameras including, for instance, charge coupled devices (CCDs) or CMOS sensors that can capture images. The data analysis component 304 can utilize the data obtained by these cameras to generate an image with depth perception that allows for focusing at various depths. The data analysis component 304 can enable stereoscopic visualization of the laryngeal aperture allowing for depth perception to improve endotracheal tube placement success. The data analysis component 304 can combine two or more images to create a composite image with depth (e.g., three dimensional), for example. Further, the data analysis component 304 can yield an output that can be transmitted, displayed, stored, matched to a pattern, etc.

It is contemplated that the data capture component(s) 302 can include any number of digital cameras. The digital camera(s) can be mounted on the articulating blade 204 and moved independently of the blade 204 allowing for improved viewing of the laryngeal opening. These cameras can collect video data and/or still image data. Further, it is contemplated that the cameras can switch between collecting video and still images, simultaneously collect video and still images, or statically collect a particular type of data. Moreover, the cameras can be high definition cameras, for example. Further, the cameras can include a heating element (e.g., coil, light emitting diode, . . . ) to mitigate fogging while positioned within the oral cavity.

The data analysis component 304 can assemble data from the data capture component(s) 302. For example, a plurality of data capture component(s) 302 can provide input data to the data analysis component 304, which can thereafter aggregate such input data to yield a unified output. According to another illustration, the data analysis component 304 can perform pattern recognition upon the data from the data capture component(s) 302 to identify whether an endotracheal tube is properly positioned, misplaced, and so forth. Further to this illustration, an indication (e.g., alarm) of the recognized state can be yielded.

According to another example, the data capture component(s) 302 can be substantially any type of sensor and/or an interface that can connect with an externally located sensor. For instance, gaseous properties (e.g., carbon dioxide levels, . . . ) can be tracked by such sensors to provide feedback associated with placement of an endotracheal tube in the esophagus of a patient; thus, the monitored carbon dioxide level can be compared to a threshold (e.g., 2-3%, substantially any other percentage of carbon dioxide, . . . ) and, if the monitored level is below the threshold, the endotracheal tube can be determined to be positioned in the esophagus. Further, any other type of property (e.g., pH level, humidity, . . . ) can be monitored by these sensors to yield similar types of feedback. Moreover, the feedback can be evaluated by the data analysis component 304 to generate an associated output.

Figure 4:
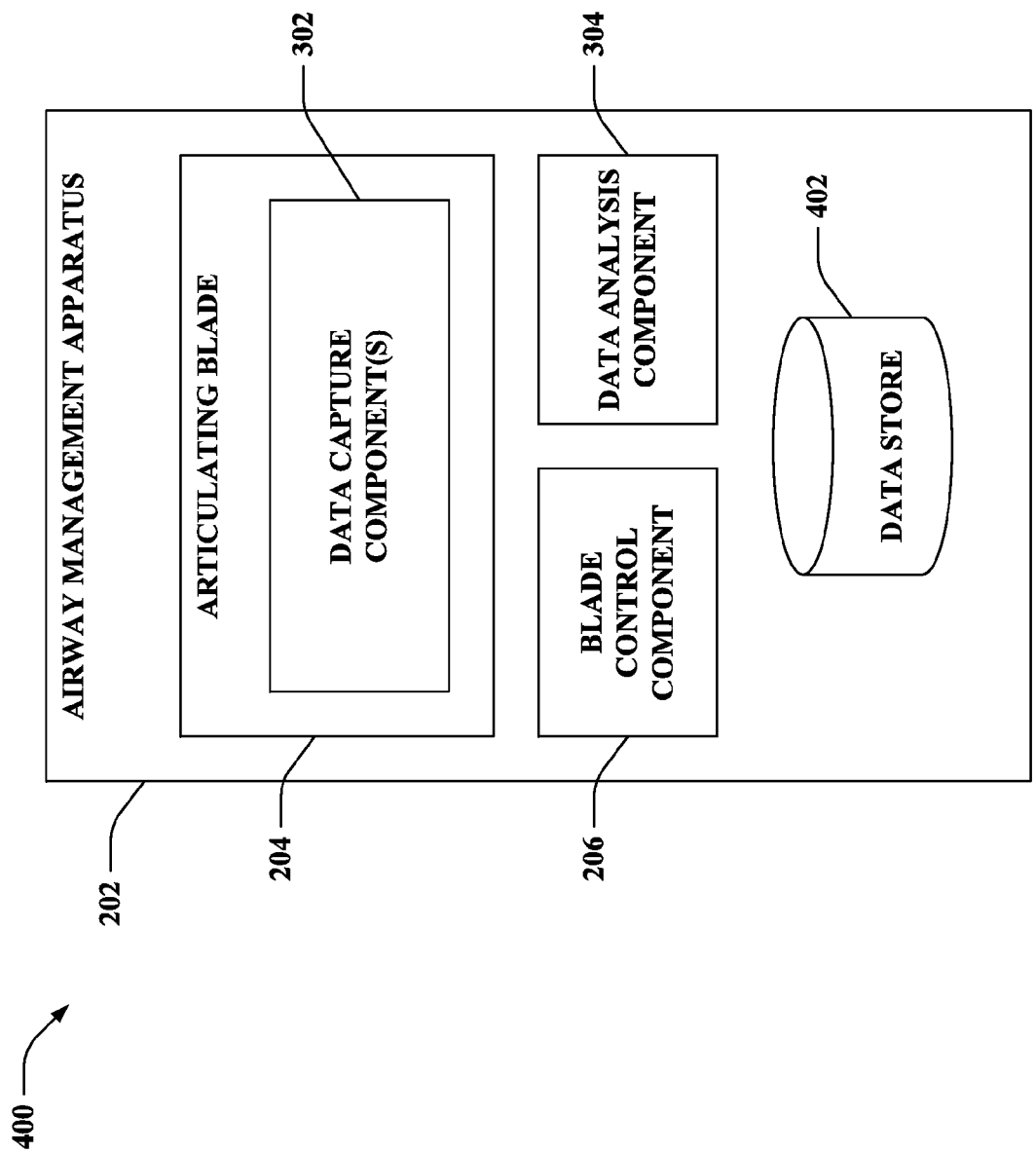
FIG. 4 illustrates a block diagram of an exemplary system that enables storing recorded data.

With reference to FIG. 4, illustrated is an example system 400 that enables storing recorded data. The system 400 includes the airway management apparatus 202, which can further comprise the articulating blade 204, the blade control component 206, and the data analysis component 304. Additionally, the articulating blade 204 can include the data capture component(s) 302. The airway management apparatus 202 can also include a data store 402 that can retain the data obtained by the data capture component(s) 302 and/or evaluated by the data analysis component 304.

The data store 402 can be, for example, either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable programmable ROM (EEPROM), or flash memory. Volatile memory can include random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), Rambus direct RAM (RDRAM), direct Rambus dynamic RAM (DRDRAM), and Rambus dynamic RAM (RDRAM). The data store 402 of the subject systems and methods is intended to comprise, without being limited to, these and any other suitable types of memory. In addition, it is to be appreciated that the data store 402 can be a server, a database, a hard drive, and the like.

By way of example, the data store 402 can be utilized to document difficult intubations. Thus, data such as images, video, alarms, and the like concerning such intubations can be retained in the data store 402. Accordingly, the data store 402 can be a flash memory chip that can be removed from the airway management apparatus 202 (e.g., from the handle) and placed in a patient's file. Additionally or alternatively, upon the airway management apparatus 202 being placed in a cradle, data retained in the data store 402 can be archived to hospital records (e.g., upon a server), printed in a report, etc. Further, the data can be archived via a wireless connection to such server. The data can be archived automatically, periodically, in response to a received request, and so forth. Further, it is contemplated that the data store 402 can similarly be included in any other type of medical device in addition to the airway management apparatus 202 to enable documenting procedures performed upon patients with these other types of medical devices.

Figure 5:
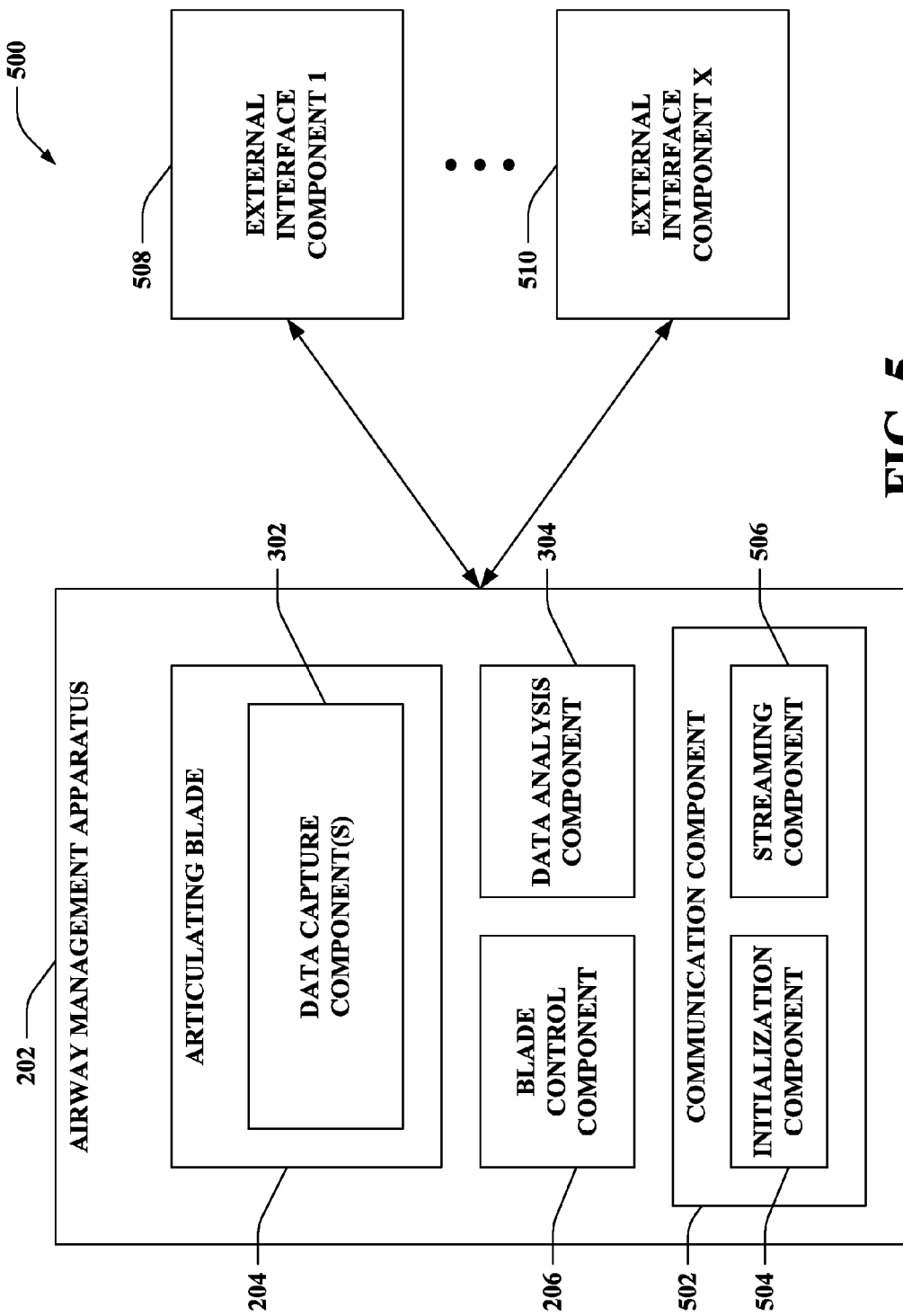
FIG. 5 illustrates a block diagram of an exemplary system that enables wirelessly transferring data captured from a laryngoscope.

Referring now to FIG. 5, illustrated is an example system 500 that enables wirelessly transferring data captured from a laryngoscope. The system 500 includes the airway management apparatus 202, which further comprises the articulating blade 204 (e.g., that further includes data capture component(s) 302), the blade control component 206, and data analysis component 304 as described above. The airway management apparatus 202 can also include a communication component 502 that can transmit and/or receive data within the system 500. The communication component 502 can further include an initialization component 504 and a streaming component 506. Moreover, the communication component 502 can enable the airway management apparatus 202 to communicate with one or more external interface components (e.g., an external interface component 1 508, . . . , an external interface component X 510, where X can be any integer).

The external interface components 508-510 can be, for example, cellular phones, smart phones, laptops, handheld communication devices, handheld computing devices, satellite radios, global positioning systems, personal digital assistants (PDAs), and/or any other suitable device. Additionally, the external interface components 508-510 can be any type of device with a monitor. The external interface components 508-510 can be located within proximity of the airway management apparatus 202. According to another example, one or more of the external interface components 508-510 can be positioned outside of a local vicinity of the airway management apparatus 202.

The initialization component 504 can determine whether any external interface components 508-510 are within range. Thus, a list of identities of these external interface components 508-510 can be populated by the initialization component 504. Thereafter, one or more of the listed external interface components 508-510 can be selected and data from the data analysis component 304 can be transmitted to the selected external interface component(s) 508-510 (e.g., which can thereafter output the data). For instance, the external interface component(s) 508-510 can visually display the output, yield audio output, and so forth.

Additionally, the initialization component 504 can allow for connecting to remotely located external interface components 508-510. For instance, the communication component 502 can enable communicating from the airway management apparatus 202 over an infrastructure based network (e.g., cellular network). Thus, a specially trained individual located anywhere in the world can be presented with feedback from the data capture component(s) 302. Further, this individual can control manipulation of the articulating blade 204 and/or the data capture component(s) 302 from the remote location.

By way of illustration, a monitor can be positioned in an operating room in which the airway management apparatus 202 is being employed. The initialization component 504 can identify that the monitor is within proximity and set up transfer of data to the monitor. For example, the monitor can automatically be initialized by the initialization component 504; thus, upon moving within range of the monitor, transmission can occur between the communication component 502 and the monitor to enable display upon the monitor of data collected by the airway management apparatus 202. Additionally or alternatively, the initialization component 504 can create a list of available devices (e.g., external interface components 508-510) including the monitor, and a selection may be made based upon a user input, a preference, a ranking, security levels, etc.

The streaming component 506 can enable real-time transfer of data from the data analysis component 304 to one or more of the external interface components 508-510. Thus, the streaming component 506 can allow for an image obtained with the data capture component(s) 302 from a patient's oral cavity to be displayed upon a PDA or any other external interface component 508-510 in real-time as the apparatus 202 is manipulated within the oral cavity. Further, the streaming component 506 can allow for the data to be transmitted to a disparate device for storage (e.g., a remotely located data store).

The communication component 502 can utilize any type of wireless technology to transfer data (e.g., WiFi, 802.11b, g, n, Bluetooth, . . . ). Thus, the communication component 502 can enable wireless digital transmission of digital images to allow for remote viewing of airway manipulation, digital recording of procedures, porting images to video equipment in place such as anesthesiology monitoring or portable handle communication devices, and so forth. Moreover, the communication component 502 can receive feedback from one or more of the external interface components 508-510; such feedback can control manipulation of the articulating blade 204 by providing a signal to the blade control component 206, for example. Also, the feedback obtained by the communication component 502 can enable moving the data capture component(s) 302 (e.g., shifting the view being captured). Accordingly, this type of feedback can enable performing telemedicine.

The system 500 can further include an intelligent component (not shown) that can be employed by the airway management apparatus 202. For example, the intelligent component can infer which external interface component 508-510 within proximity to display data upon. Pursuant to another example, the intelligent component can infer potential errors in use associated with the airway management apparatus 202 (e.g., misplaced endotracheal tube, . . . ) and yield a corresponding alarm.

It is to be understood that the intelligent component can provide for reasoning about or infer states of the system, environment, and/or user from a set of observations as captured via events and/or data. Inference can be employed to identify a specific context or action, or can generate a probability distribution over states, for example. The inference can be probabilistic—that is, the computation of a probability distribution over states of interest based on a consideration of data and events. Inference can also refer to techniques employed for composing higher-level events from a set of events and/or data. Such inference results in the construction of new events or actions from a set of observed events and/or stored event data, whether or not the events are correlated in close temporal proximity, and whether the events and data come from one or several event and data sources. Various classification (explicitly and/or implicitly trained) schemes and/or systems (e.g., support vector machines, neural networks, expert systems, Bayesian belief networks, fuzzy logic, data fusion engines . . . ) can be employed in connection with performing automatic and/or inferred action in connection with the claimed subject matter.

A classifier is a function that maps an input attribute vector, $x=(x1, x2, x3, x4, xn)$, to a confidence that the input belongs to a class, that is, $f(x)=confidence(class)$. Such classification can employ a probabilistic and/or statistical-based analysis (e.g., factoring into the analysis utilities and costs) to prognose or infer an action that a user desires to be automatically performed. A support vector machine (SVM) is an example of a classifier that can be employed. The SVM operates by finding a hypersurface in the space of possible inputs, which hypersurface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

Figure 6:
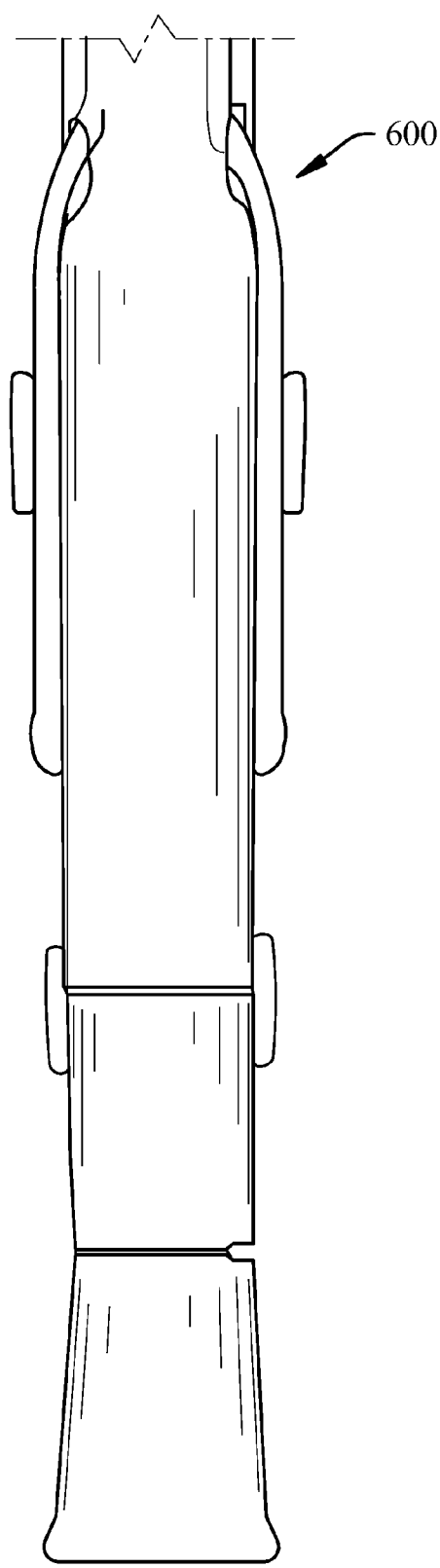
FIG. 6 illustrates another example schematic of an airway management apparatus in accordance with various aspects of the claimed subject matter.
Figure 7:
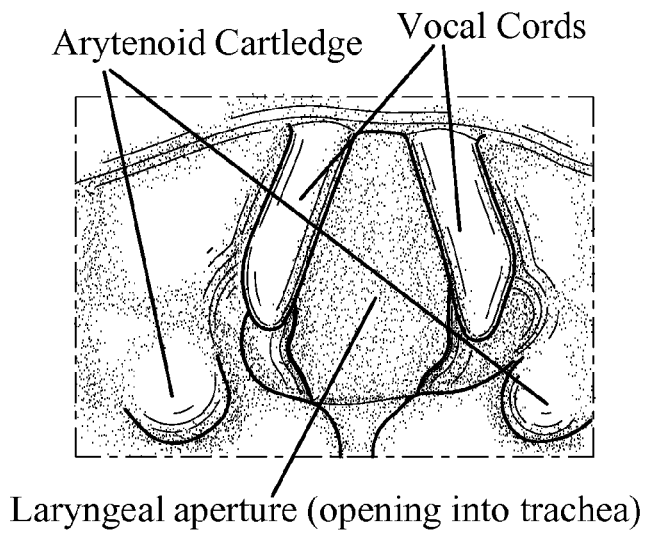
FIGS. 7 and 8 illustrate the vocal cords and laryngeal aperture.
Figure 8:
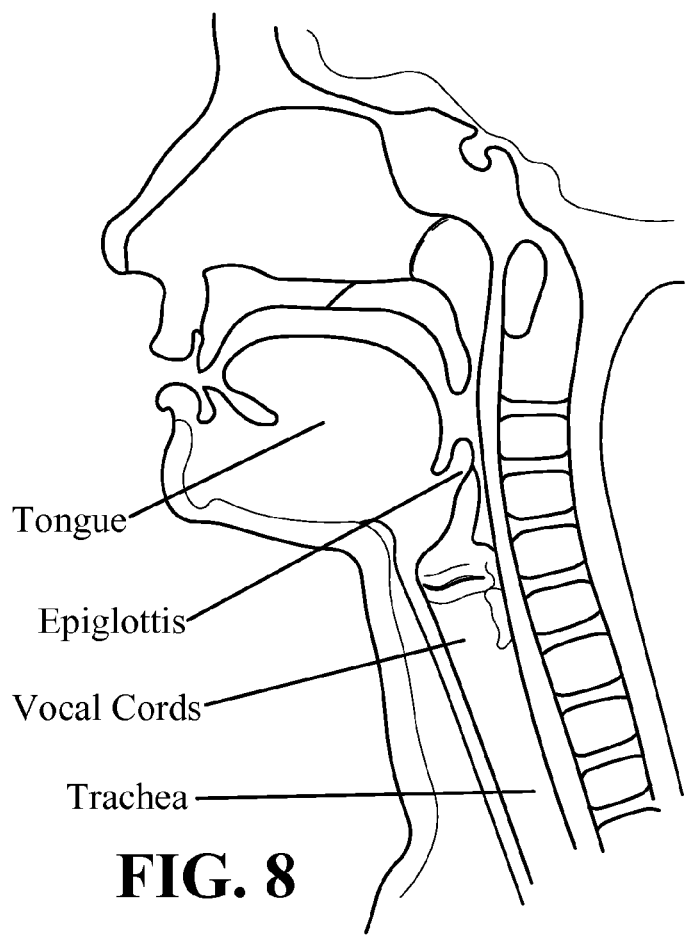
Figure 9:
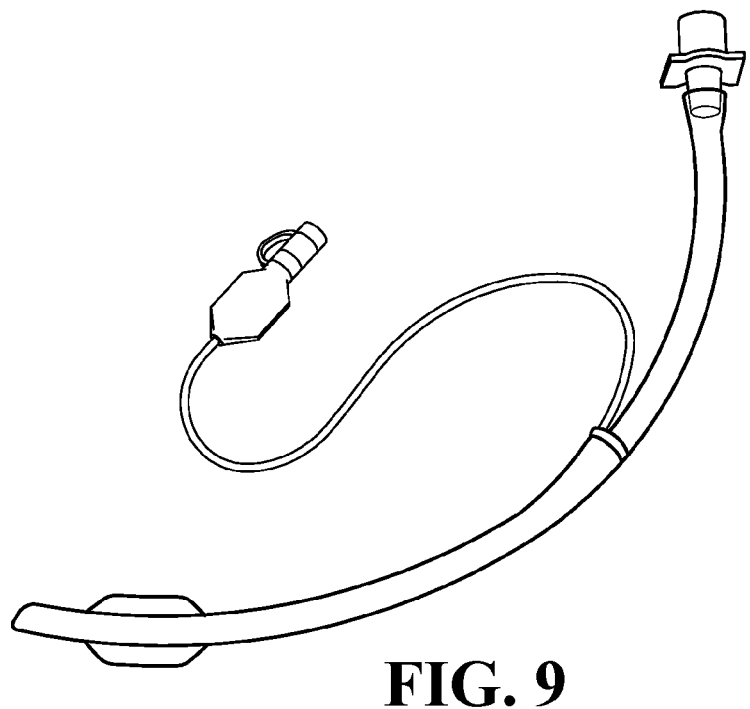
FIG. 9 illustrates an example endotracheal tube that can be utilized in connection with the airway management apparatus described herein.
Figure 10:
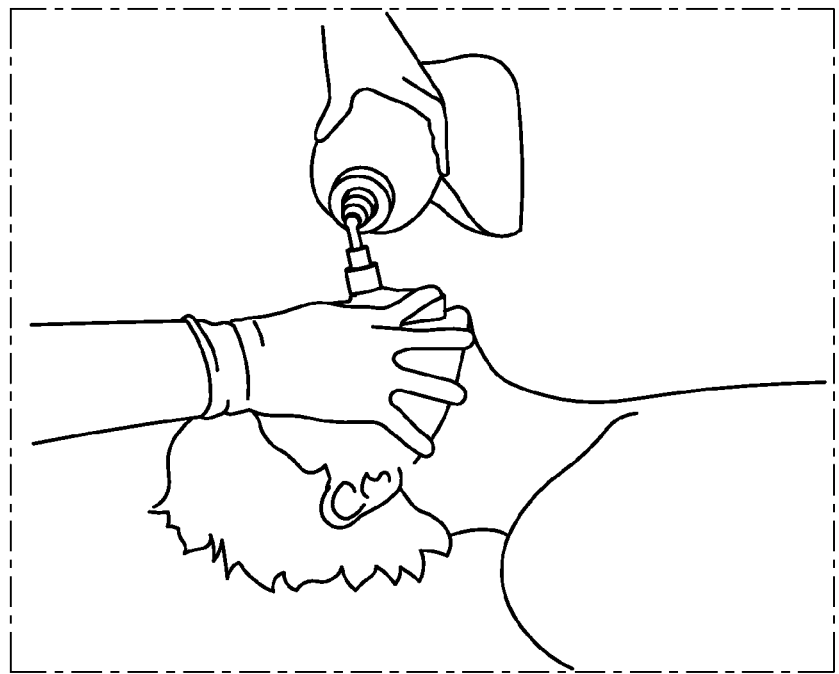
FIG. 10 illustrates bag-mask ventilation.

Referring to FIG. 6, illustrated is another example schematic of an airway management apparatus 600. The schematic shown in FIG. 6 is a top view of the schematic depicted in FIG. 1. FIGS. 7 and 8 depict the vocal cords and laryngeal aperture. FIG. 9 illustrates an example endotracheal tube that can be utilized in connection with the airway management apparatus described herein. FIG. 10 illustrates bag-mask ventilation.

A typical example operating room intubation scenario proceeds as follows. A patient who is spontaneously breathing on their own is placed in a supine position and supplemental oxygen is provided in an attempt to "fill" their lungs, blood, and tissues with higher than normal oxygen levels, hyperoxygenation. This is done to prevent a fall in oxygen levels, deaturation or the oxygen carrying molecules hemoglobin in the blood, during the period when the patient is not breathing as a result of the administration of anesthetic drugs that render patients unconscious and apneic (not breathing on their own) and the initiation of mechanical ventilation through the properly placed endotracheal tube. Typically, with hyperoxygenation, an anesthesiologist has about 2-3 minutes to place the endotracheal tube into the trachea before the patient becomes hypoxic requiring the addition of supplemental oxygen delivered with bag-mask ventilation (as shown in FIG. 10). In certain situations, a failure to place the endotracheal tube into the trachea and start mechanical ventilation, bag-mask ventilation is extremely difficult or not possible resulting in severe hypoxia and potentially death or irreversible brain damage. These delays in securing an airway with the proper placement of an endotracheal tube extend the amount and time of anesthesia and add potential physiologic derangements that are poorly tolerated in certain patient populations, especially the elderly.

Complications with placement of an endotracheal tube do not end with visualization of the opening to the trachea. Placement of a rigid laryngoscope into someone's mouth and using this to forcefully move the tongue, lower jaw, and upper airway soft tissue out of the way is very stimulation and not reliably blunted with standard anesthetic induction medications. Endotracheal intubation can result in severe physiologic stresses in patient's that often lead to increases in heart rate and blood pressure in the adult population, and a precipitous fall in heart rate in pediatric patients. These stresses are not well tolerated in certain patient groups with co-existing heart conditions or those already at physiologic extremes (such as trauma patients).

If one starts with a patient who is spontaneously breathing and oxygenating themselves, which pertains to the majority of patients taken to the operating room for elective procedures, it is assumed they will be amenable to the placement of an endotracheal tube once anesthesia is administered, provided a comprehensive airway evaluation does not uncover any potential problems. Once anesthesia is administered, a once patent airway can become compromised by a relaxation of the upper airway musculature resulting in an obstruction that can be very difficult to overcome with bag-mask ventilation or the use of other airway devices. In these patients, a once patent airway when they were awake can now require immediate placement of an endotracheal tube into a trachea that is remote to the anesthesiologist. As described herein, the development of endoscopic equipment including small, high resolution cameras and the ability to digitalize and transmit an image has the potential to improve the viewing of the laryngeal aperture resulting in an easier, quicker, less traumatic and with reduced physiologic perturbations in patients undergoing general anesthetic as well as those requiring intubation for some other emergency medical condition elsewhere inside or outside the hospital. To date, typical devices have been unable to overcome the problems encountered in conventional laryngoscopy and intubation.

Various types of endoscopic equipment are routinely being used in many areas of medicine and surgery. These devices can be ridged or flexible and typically consist of a system to deliver a high intensity light beam to the area to be visualized. This light delivery is usually in the form of a fiberoptic cable. Most of these devices also use an external cable to connect the endoscopic device to some external power/light generating source by an additional cable. The camera at the tip of the endoscopic device can consist of a CCD (charge coupled device) sensor, in the form of a light sensitive chip that converts an optical source into an electrical one, or an array of fiberoptic cables coherently aligned to deliver the light encoded image back to some video display system through an external cable connection.

The ubiquitous use of endoscopic equipment in the health care system today has resulted in some sophisticated equipment; however, the series of interconnected cables makes these devices difficult to maneuver in the best situations, severely complicating and emergency situation or a procedure performed outside a well controlled environment. In addition, the fragility of fiberoptic bundles results in frequent and easy damage of these cables adding to the escalating health care costs. Relatively minimal damage to the fiberoptic bundles leads to a degradation in image quality that is unusable for the delicate medical procedures the endoscope was designed for.

In light of all of these problems, it is desirable to provide a video laryngoscopic system that is easy to use, adaptable to the wide variation in normal and abnormal upper airway pathology we see every day in the hospital, facilitates easy placement into a patients oral cavity with little or no stimulation, and allows for the transmission of a digital image to any number of video monitoring systems using wireless technology in place of external cable connections.

The ability to easily articulate a laryngoscopic blade that has already been placed into someone's oral cavity allows for utilizing a single device across a wide spectrum of normal and abnormal anatomic situations. Coupled with an articulating blade, a coherently adapting channel to guide the endotracheal tube to the exact position where the camera is looking is required to place the endotracheal tube and not just visualize where it needs to go.

In certain airway situations, the placement of an endotracheal can only safely be accomplished by keeping a patient in an awake state and spontaneously breathing. In these situations, is it of paramount importance that one is able to adequately anesthetize the upper airway to blunt the cough reflex as well as to blunt any painful stimuli these patients would experience with the placement of the intubation equipment. A single airway device that takes all of these situations into account would decrease the time required for intubation, decrease the stress on the patient, and reduce the cost of equipment as well as equipment processing time and expense.

The aforementioned objectives can be achieved with a completely redesigned laryngoscopic blade, an integrated digital stereoscopic camera and high intensity, low power light source and light conducting system, the addition of a liquid, atomizing device for the delivery of local anesthetic or humidification to the airway mucosa, a specialized, dynamically sizing channel that adapts to the contour of the laryngoscopic blade allowing for the delivery of an endotracheal tube or other airway device to the exact position of the camera view.

Figure 11:
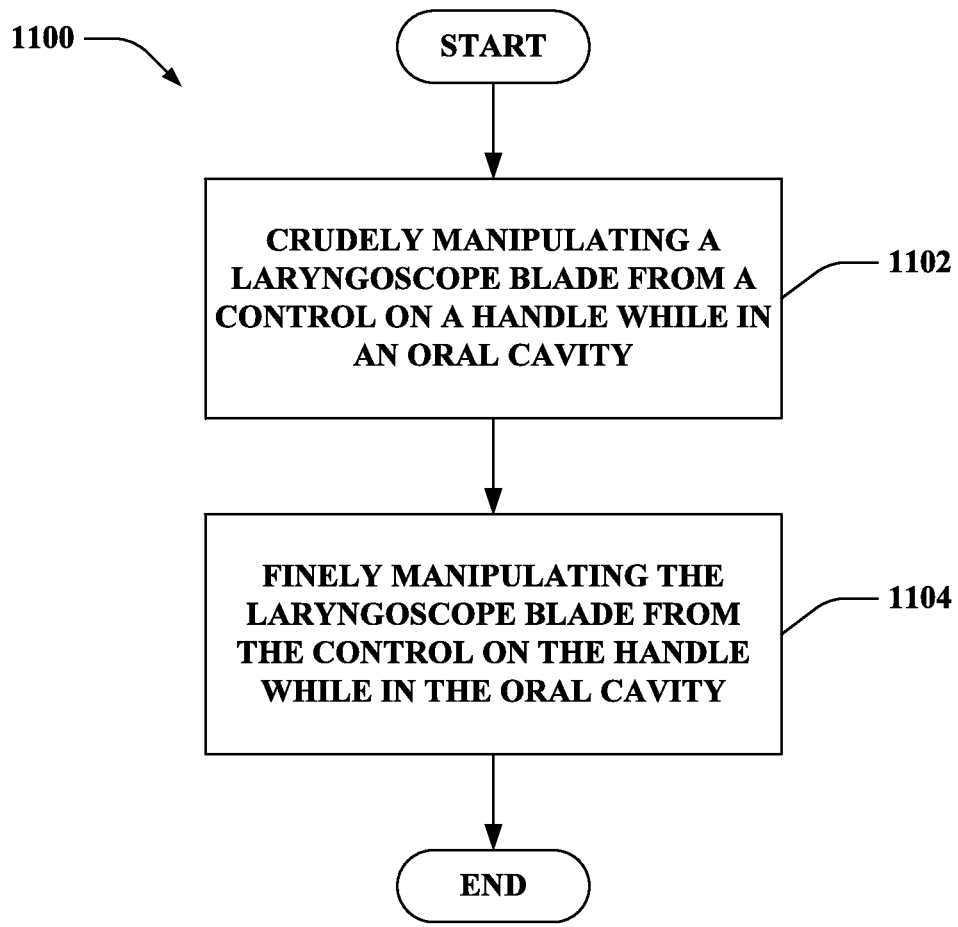
FIG. 11 illustrates an exemplary methodology that enables utilizing a laryngoscope with an articulating blade.
Figure 12:
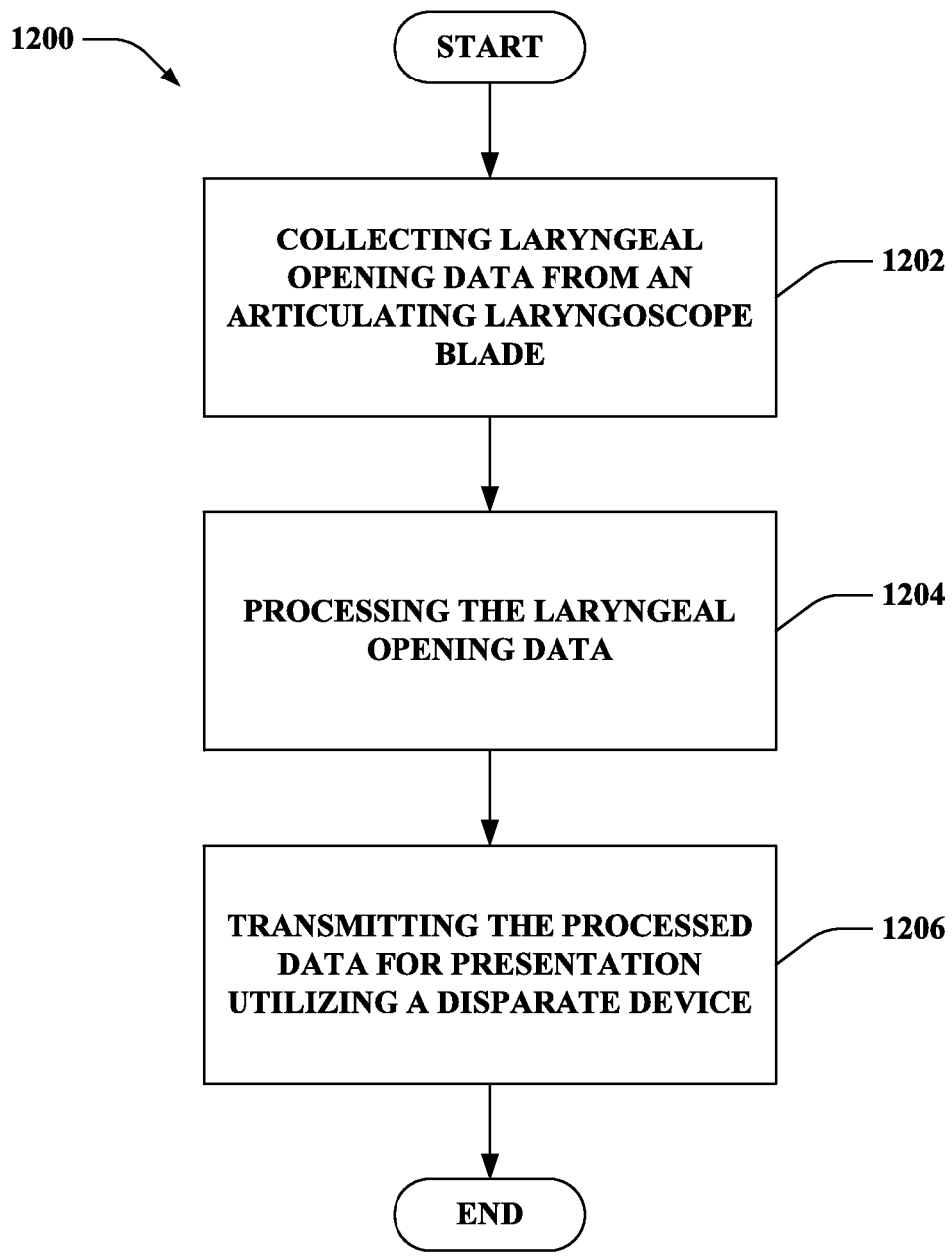
FIG. 12 illustrates an exemplary methodology that facilitates presenting data related to intubation upon an external device in real time.

FIGS. 11-12 illustrate methodologies in accordance with the claimed subject matter. For simplicity of explanation, the methodologies are depicted and described as a series of acts. It is to be understood and appreciated that the subject innovation is not limited by the acts illustrated and/or by the order of acts, for example acts can occur in various orders and/or concurrently, and with other acts not presented and described herein. Furthermore, not all illustrated acts may be required to implement the methodologies in accordance with the claimed subject matter. In addition, those skilled in the art will understand and appreciate that the methodologies could alternatively be represented as a series of interrelated states via a state diagram or events.

Referring to FIG. 11, illustrated is a methodology 1100 that enables utilizing a laryngoscope with an articulating blade. At 1102, a laryngoscope blade can be crudely manipulated from a control on a handle while in an oral cavity. The laryngoscope blade can be articulated to position one or more cameras included with the laryngoscope blade (e.g., incorporated into the blade, mounted upon the blade, . . . ) at the base of the tongue looking upwards towards the vocal cords. In contrast to conventional techniques where manipulation of the blade is conducted while outside of the oral cavity, manipulation of the laryngoscope blade can occur within the oral cavity in connection with the claimed subject matter; thus, repeated removal and reinsertion of the blade can be mitigated. At 1104, the laryngoscope blade can be finely manipulated from the control on the handle while in the oral cavity. The fine articulation, for example, can enable moving a tip of the blade to move the epiglottis, thereby yielding a clearer view of the vocal cords. It is contemplated that the crude and fine manipulation of the laryngoscope blade can be effectuated mechanically, via an electric signal, and so forth.

Turning to FIG. 12, illustrated is a methodology 1200 that facilitates presenting data related to intubation upon an external device in real time. At 1202, laryngeal opening data can be collected from an articulating laryngoscope blade. For example, data can be obtained utilizing digital cameras mounted upon and/or incorporated into the articulating laryngoscope blade. Further, the blade can be maneuvered to position the cameras with a clear view to the vocal cords. At 1204, the laryngeal opening data can be processed. For instance, data from a plurality of digital cameras can be combined to yield a stereoscopic view of the vocal cords. At 1206, the processed data can be transmitted for presentation utilizing a disparate device. The data can be transmitted wirelessly, for instance. Moreover, the processed data can be transferred to any type of disparate device that can yield an output. Thus, for example, the processed data can be sent wirelessly to a monitor in an operating room, a cell phone, a PDA, etc. Further, the disparate device can render an output in real time. Accordingly, as the laryngoscope blade is articulated within the oral cavity, a display can be rendered upon the disparate device in real time that shows a view of the vocal cords from the base of the tongue.

Figure 13:
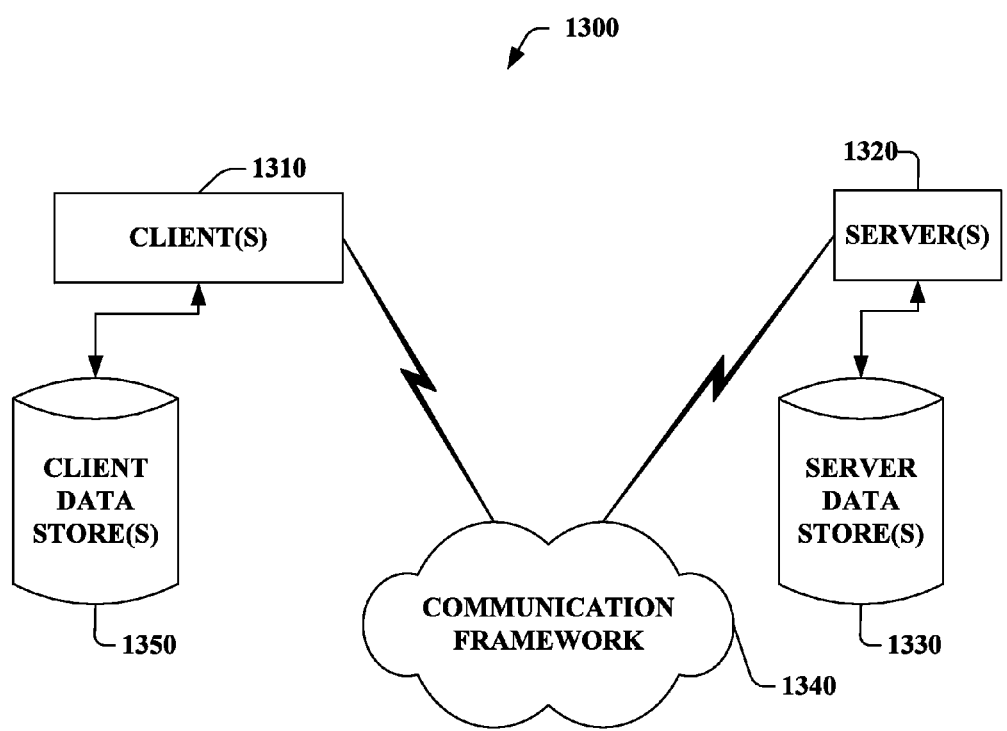
FIG. 13 illustrates an exemplary networking environment, wherein the novel aspects of the claimed subject matter can be employed.
Figure 14:
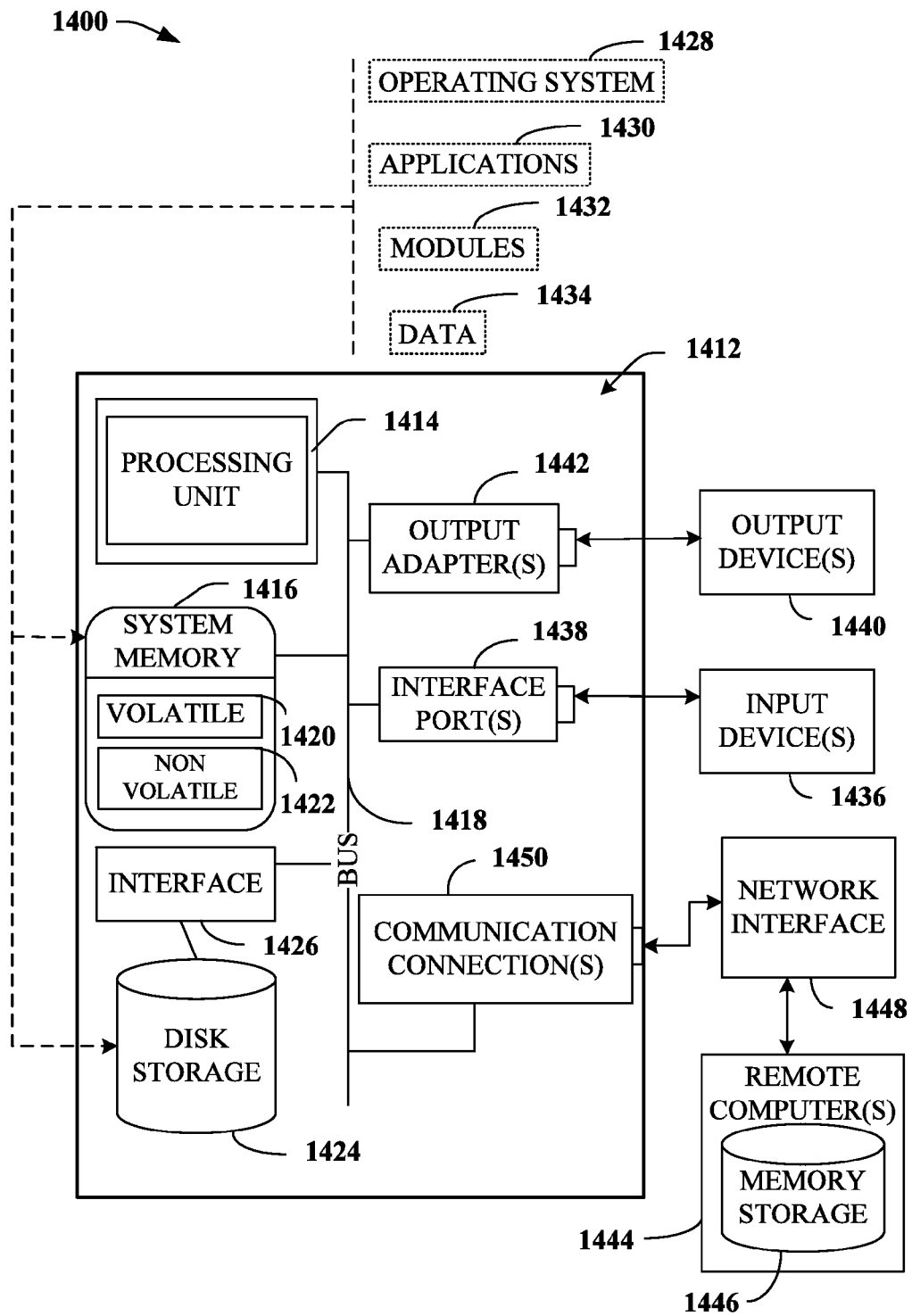
FIG. 14 illustrates an exemplary operating environment that can be employed in accordance with the claimed subject matter.

In order to provide additional context for implementing various aspects of the claimed subject matter, FIGS. 13-14 and the following discussion is intended to provide a brief, general description of a suitable computing environment in which the various aspects of the subject innovation may be implemented. For instance, FIGS. 13-14 set forth a suitable computing environment that can be employed in connection with generating and/or utilizing replicas of states. While the claimed subject matter has been described above in the general context of computer-executable instructions of a computer program that runs on a local computer and/or remote computer, those skilled in the art will recognize that the subject innovation also may be implemented in combination with other program modules. Generally, program modules include routines, programs, components, data structures, etc., that perform particular tasks and/or implement particular abstract data types.

Moreover, those skilled in the art will appreciate that the inventive methods may be practiced with other computer system configurations, including single-processor or multi-processor computer systems, minicomputers, mainframe computers, as well as personal computers, hand-held computing devices, microprocessor-based and/or programmable consumer electronics, and the like, each of which may operatively communicate with one or more associated devices. The illustrated aspects of the claimed subject matter may also be practiced in distributed computing environments where certain tasks are performed by remote processing devices that are linked through a communications network. However, some, if not all, aspects of the subject innovation may be practiced on stand-alone computers. In a distributed computing environment, program modules may be located in local and/or remote memory storage devices.

FIG. 13 is a schematic block diagram of a sample-computing environment 1300 with which the claimed subject matter can interact. The system 1300 includes one or more client(s) 1310. The client(s) 1310 can be hardware and/or software (e.g., threads, processes, computing devices). The system 1300 also includes one or more server(s) 1320. The server(s) 1320 can be hardware and/or software (e.g., threads, processes, computing devices). The servers 1320 can house threads to perform transformations by employing the subject innovation, for example.

One possible communication between a client 1310 and a server 1320 can be in the form of a data packet adapted to be transmitted between two or more computer processes. The system 1300 includes a communication framework 1340 that can be employed to facilitate communications between the client(s) 1310 and the server(s) 1320. The client(s) 1310 are operably connected to one or more client data store(s) 1350 that can be employed to store information local to the client(s) 1310. Similarly, the server(s) 1320 are operably connected to one or more server data store(s) 1330 that can be employed to store information local to the servers 1320.

With reference to FIG. 14, an exemplary environment 1400 for implementing various aspects of the claimed subject matter includes a computer 1412. The computer 1412 includes a processing unit 1414, a system memory 1416, and a system bus 1418. The system bus 1418 couples system components including, but not limited to, the system memory 1416 to the processing unit 1414. The processing unit 1414 can be any of various available processors. Dual microprocessors and other multiprocessor architectures also can be employed as the processing unit 1414.

The system bus 1418 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 1394), and Small Computer Systems Interface (SCSI).

The system memory 1416 includes volatile memory 1420 and nonvolatile memory 1422. The basic input/output system (BIOS), containing the basic routines to transfer information between elements within the computer 1412, such as during start-up, is stored in nonvolatile memory 1422. By way of illustration, and not limitation, nonvolatile memory 1422 can include read only memory (ROM), programmable ROM (PROM), electrically programmable ROM (EPROM), electrically erasable programmable ROM (EEPROM), or flash memory. Volatile memory 1420 includes random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), Rambus direct RAM (RDRAM), direct Rambus dynamic RAM (DRDRAM), and Rambus dynamic RAM (RDRAM).

Computer 1412 also includes removable/non-removable, volatile/non-volatile computer storage media. FIG. 14 illustrates, for example a disk storage 1424. Disk storage 1424 includes, but is not limited to, devices like a magnetic disk drive, floppy disk drive, tape drive, Jaz drive, Zip drive, LS-100 drive, flash memory card, or memory stick. In addition, disk storage 1424 can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 1424 to the system bus 1418, a removable or non-removable interface is typically used such as interface 1426.

It is to be appreciated that FIG. 14 describes software that acts as an intermediary between users and the basic computer resources described in the suitable operating environment 1400. Such software includes an operating system 1428. Operating system 1428, which can be stored on disk storage 1424, acts to control and allocate resources of the computer system 1412. System applications 1430 take advantage of the management of resources by operating system 1428 through program modules 1432 and program data 1434 stored either in system memory 1416 or on disk storage 1424. It is to be appreciated that the claimed subject matter can be implemented with various operating systems or combinations of operating systems.

A user enters commands or information into the computer 1412 through input device(s) 1436. Input devices 1436 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1414 through the system bus 1418 via interface port(s) 1438. Interface port(s) 1438 include, for example, a serial port, a parallel port, a game port, and a universal serial bus (USB). Output device(s) 1440 use some of the same type of ports as input device(s) 1436. Thus, for example, a USB port may be used to provide input to computer 1412, and to output information from computer 1412 to an output device 1440. Output adapter 1442 is provided to illustrate that there are some output devices 1440 like monitors, speakers, and printers, among other output devices 1440, which require special adapters. The output adapters 1442 include, by way of illustration and not limitation, video and sound cards that provide a means of connection between the output device 1440 and the system bus 1418. It should be noted that other devices and/or systems of devices provide both input and output capabilities such as remote computer(s) 1444.

Computer 1412 can operate in a networked environment using logical connections to one or more remote computers, such as remote computer(s) 1444. The remote computer(s) 1444 can be a personal computer, a server, a router, a network PC, a workstation, a microprocessor based appliance, a peer device or other common network node and the like, and typically includes many or all of the elements described relative to computer 1412. For purposes of brevity, only a memory storage device 1446 is illustrated with remote computer(s) 1444. Remote computer(s) 1444 is logically connected to computer 1412 through a network interface 1448 and then physically connected via communication connection 1450. Network interface 1448 encompasses wire and/or wireless communication networks such as local-area networks (LAN) and wide-area networks (WAN). LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1450 refers to the hardware/software employed to connect the network interface 1448 to the bus 1418. While communication connection 1450 is shown for illustrative clarity inside computer 1412, it can also be external to computer 1412. The hardware/software necessary for connection to the network interface 1448 includes, for exemplary purposes only, internal and external technologies such as, modems including regular telephone grade modems, cable modems and DSL modems, ISDN adapters, and Ethernet cards.

What has been described above includes examples of the subject innovation. It is, of course, not possible to describe every conceivable combination of components or methodologies for purposes of describing the claimed subject matter, but one of ordinary skill in the art may recognize that many further combinations and permutations of the subject innovation are possible. Accordingly, the claimed subject matter is intended to embrace all such alterations, modifications, and variations that fall within the spirit and scope of the appended claims.

In particular and in regard to the various functions performed by the above described components, devices, circuits, systems and the like, the terms (including a reference to a "means") used to describe such components are intended to correspond, unless otherwise indicated, to any component which performs the specified function of the described component (e.g., a functional equivalent), even though not structurally equivalent to the disclosed structure, which performs the function in the herein illustrated exemplary aspects of the claimed subject matter. In this regard, it will also be recognized that the innovation includes a system as well as a computer-readable medium having computer-executable instructions for performing the acts and/or events of the various methods of the claimed subject matter.

In addition, while a particular feature of the subject innovation may have been disclosed with respect to only one of several implementations, such feature may be combined with one or more other features of the other implementations as may be desired and advantageous for any given or particular application. Furthermore, to the extent that the terms "includes," and "including" and variants thereof are used in either the detailed description or the claims, these terms are intended to be inclusive in a manner similar to the term "comprising."

What is claimed is:

1. An airway management apparatus, comprising:
   an articulating blade comprising a plurality of articulation points, the plurality of articulation points comprise at least a first articulation point that alters a curvature associated with the articulating blade and a second articulation point that manipulates a tip of the articulating blade;
   a camera mounted on the articulating blade, wherein the camera moves independently of the articulating blade; and
   a blade control component that controls manipulation of the articulating blade at one or more of the plurality of articulation points.

2. The apparatus of claim 1, the camera being a digital camera.

3. The apparatus of claim 1, wherein the camera is configured to view a laryngeal opening.

4. The apparatus of claim 1, the camera comprises a heating element to mitigate fogging.

5. The apparatus of claim 1, further comprising another camera, wherein the camera and the other camera enable stereoscopic visualization of a laryngeal aperture while providing depth perception.

6. The apparatus of claim 5, further comprising a data store that retains the data obtained by the camera and the other camera.

7. The apparatus of claim 6, wherein the data store is removable flash memory.

8. The apparatus of claim 5, further comprising a communication component that transfers data obtained by at least one of the camera and the other camera to a disparate device, wherein the disparate device outputs the data in real time.

9. The apparatus of claim 8, further comprising an initialization component that identifies disparate devices within range and enables selection of one or more of the identified disparate devices for directing data transmission.

10. The apparatus of claim 8, the communication component receives control signals from the disparate device, the control signals being utilized by the blade control component to manipulate the articulating blade.

11. The apparatus of claim 1, further comprising an adaptable channel that secures and enables directional placement of an endotracheal tube or intubation stylet into a trachea under direct vision.

12. The apparatus of claim 1, further comprising a handle that connects to the articulating blade, the handle comprises a power source or a light transmission system.

\* \* \* \* \*